(12) United States Patent
Parasrampuria et al.

(10) Patent No.: US 7,045,513 B1
(45) Date of Patent: May 16, 2006

(54) DHEA COMPOSITION AND METHOD

(75) Inventors: Jagdish Parasrampuria, Bridgewater, NJ (US); Maxine B. Yonker, Emerald Hills, CA (US); Kenneth E. Schwartz, San Mateo, CA (US); Marc J. Gurwith, Los Altos, CA (US)

(73) Assignee: Genelabs Technologies, Inc., Redwood City, CA (US)

( * ) Notice: Subject to any disclaimer, the term of this patent is extended or adjusted under 35 U.S.C. 154(b) by 871 days.

(21) Appl. No.: 09/526,802

(22) Filed: Mar. 16, 2000

Related U.S. Application Data (60) Provisional application No. 60/125,201, filed on Mar. 18, 1999.

(51) Int. Cl.
*A61K 31/56* (2006.01)

(52) U.S. Cl. ............ 514/170; 514/169; 514/177; 514/178; 514/180

(58) Field of Classification Search ........... 514/169, 514/178, 179, 182, 170, 171, 177, 180
See application file for complete search history.

(56) References Cited

U.S. PATENT DOCUMENTS

| | | | | | |
|---|---|---|---|---|---|
| 5,077,284 | A | * | 12/1991 | Loria et al. ............ | 514/169 |
| 5,407,927 | A | * | 4/1995 | Morales et al. .......... | 514/177 |
| 5,728,688 | A | * | 3/1998 | Labrie ................ | 514/178 |
| 5,776,923 | A | * | 7/1998 | Labrie ................ | 514/176 |
| 5,780,460 | A | * | 7/1998 | Labrie ................ | 514/178 |
| 5,824,671 | A | * | 10/1998 | Labrie ................ | 514/178 |
| 5,837,700 | A | * | 11/1998 | Labrie ................ | 514/178 |

FOREIGN PATENT DOCUMENTS

| EP | 0389035 | 3/1990 |
|---|---|---|
| EP | 0389035 A | 9/1990 |

OTHER PUBLICATIONS

Chang et al. (DN 123:265915, HCAPLUS, abstract of J. Pharm. Sci. (1995), 84(10), 1169-79).*
Chang, Luh-Chian et al., "Solid State Characterization of Dehydroepiandrosterone," Journal of Pharmaceutical Sciences 84:10:1169-1179 (Oct. 1995).
Yu, Lian et al., "Physical Characterization of Polymorphic Drugs: An Integrated Characterization Strategy," PSTT 1:3:118-127 (Jun. 1998).
Merck: "The Merck Index," USA XP002148233, p. 1323 (1996).
Arit, W., et al., *J. Clin. Endocrinol. Metab. 83* (6):1928-1934 (1998).
Barker, E.V. et al., *Endocrinology 134*:982-989 (1994).
Barrett-Connor et al., *New Engl. J. Med. 315*:1519 (1986).
Caira, M.R. et al., *J. Chem. Crystallogr. 25*:393 (1995).
Chang, L.C. et al. *J. Pharmaceut. Sci. 84*:1169-1179 (1995).
Comer, K.A. and Falany, C.N., *Mol. Pharmacol. 41*:645-651 (1992).
Cox, P.J. et al., *Acta Crystallogr.* C46, 334-336 (1990).
Falany, C.N. et al., *Ann. NY Acad. Sci. 774*:59-72 (1995).
Frye and Maciel, *J. Mag. Res. 48*:125 (1982).
Grodin, J.M. et al., *J. Clin. Endo. Metab. 36*:207-214 (1973).
Lachelin, G.C. et al., *J. Clin. Endocrinol. Metab. 49* (6):892-898 (1979).
Longcope, C., *Ann. NY Acad. Sci. 774*:143-148 (1995).
MacDonald, J.C. *J. Mag. Res.* 38:381 (1980).
Meikle, A.W. et al., *J. Steroid Biochem. Molec. Biol.* 293-304 (1992).
Merck, *The Merck Index* 1996, Merck, NJ, USA XP002148233.
Orentreich, N. et al, *J. Clin. Endocrinol. Metab. 59*:551-555 (1984).
Van Cauter, E., *Horm. Res. 32*(2):45-53 (1990).
Yen, S.S. et al., *Ann. NY Acad. Sci. 774*: 128-142 (1995).
Yu, L. (Reprint) et al. *Pharmaceutical Science & Technology Today* vol. 1., No. 3 pp. 118-127 (Jun., 1998).

* cited by examiner

*Primary Examiner*—Sabiha Qazi
(74) *Attorney, Agent, or Firm*—Quine I.P. Law Group, P.C.; Emily M. Haliday (57) ABSTRACT

Disclosed are improved pharmaceutical formulations comprising dehydroepiandrosterone (DHEA), enriched in selected polymorphic forms, for therapeutic applications. In one embodiment, the formulation comprises, in solid form, DHEA, at least 85% of which is present as a single polymorph selected from the form I polymorph or the form II polymorph, and at least one pharmaceutical excipient. Methods for making and using such compositions are also disclosed.

14 Claims, 4 Drawing Sheets

Fig. 1

Mean Baseline Adjusted DHEA Concentrations

Fig. 2

Mean Baseline Adjusted DHEA-S Concentrations

DHEA COMPOSITION AND METHOD

DHEA COMPOSITION AND METHOD

This application claims priority to U.S. provisional application Ser. No. 60/125,201, filed Mar. 18, 1999, which is hereby incorporated by reference in its entirety.

FIELD OF THE INVENTION

The present invention provides pharmaceutical formulations of DHEA enriched for polymorph form I or form II, which are useful for various therapeutic applications. In particular, the invention is directed to formulations of DHEA having more consistent bioavailability than previously used formulations.

REFERENCES

Arlt, W. et al., *J. Clin. Endocrinol. Metab.* 83(6):1928–1934 (1998).
Barker, E. V. et al., *Endocrinology* 134:982–989 (1994).
Barrett-Connor et al., *New Engl. J. Med.* 315:1519 (1986).
Caira, M. R. et al., *J. Chem. Crystallogr.* 25:393 (1995).
Chang, L. C. et al., *J. Pharmaceut. Sci.* 84:1169–1179 (1995).
Comer, K. A. and Falany, C. N., *Mol. Pharmacol.* 41:645–651 (1992).
Cox, P. J. et al., *Acta Crystallogr.* C46, 334–336 (1990).
Falany, C. N. et al., *Ann. NY Acad. Sci.* 774:59–72 (1995).
Frye and Maciel, *J. Mag. Res.* 48:125 (1982).
Grodin, J. M. et al., *J. Clin. Endo. Metab.* 36:207–214 (1973).
GUIDANCE FOR INDUSTRY: *Q2B VALIDATION OF ANALYTICAL PROCEDURES: METHODOLOGY*, HFD-210, CDER, Rockville, Md.
Kuhnert-Brandstätter, M., *THERMOMICROSCOPY IN THE ANALYSIS OF PHARMACEUTICALS*, Pergamon Press, Oxford, U.K. (1971).
Lacheline, G. C. et al., *J. Clin. Endocrinol. Metab.* 49(6):892–898 (1979).
Longcope, C., *Ann. NY Acad. Sci.* 774:143–148 (1995).
MacDonald, J. C., *J. Mag. Res.* 38:381 (1980).
Meikle, A. W. et al., *J. Steroid Biochem. Molec. Biol.* 293–304 (1992).
Orentreich, N. et al., *J. Clin. Endocrinol. Metab.* 59:551–555 (1984).
van Cauter, E., *Horm. Res.* 32(2):45–53 (1990).
Yen, S. S. et al., *Ann. NY Acad. Sci.* 774:128–142 (1995).

BACKGROUND OF THE INVENTION

Dehydroepiandrosterone (DHEA), also known as 3-beta-hydroxyandrost-5-en-17-one, dehydroisoandrosterone, trans-dehydroandrosterone, $\Delta^5$-androsten-3-$\beta$-ol-17-one, and prasterone, is a naturally occurring intermediate formed in the course of synthesis of various steroids from cholesterol. DHEA is the most abundant steroid hormone in humans and is produced mainly by the adrenal cortex as an inactive sulfate ester (DHEA-S). DHEA production also occurs in the testes, ovaries, and brain. After achieving a plateau level during early adulthood (ages 16 to 24), total serum DHEA (DHEA+DHEA-S) declines steadily to about 5 to 10% of peak values by age 60 to 70 (Orentreich et al., 1984).

DHEA has been proposed for use in treating many medical conditions, such as systemic lupus erythematosus (U.S. Pat. No. 5,817,650), primary adrenal insufficiency (U.S. Pat. No. 5,861,391), Addison's disease (ibid.), reduced libido (U.S. Pat. No. 5,855,548), obesity (U.S. Pat. No. 5,846,962), osteoporosis (U.S. Pat. Nos. 5,846,960 and 5,855,548), and fibromyalgia (U.S. Pat. No. 5,935,949). DHEA can be administered by various routes and is orally active.

The pharmacokinetics of exogenously administered DHEA are complicated by endogenous production of DHEA and by the reversible interconversion between DHEA and DHEA-S, the major metabolite of DHEA, which acts as a reservoir for DHEA. DHEA exhibits wide diurnal variations in endogenous production, while DHEA-S levels show little variation during the day. Changes in plasma DHEA occur in parallel to those of ACTH and cortisol, with an early morning maximum, declining levels through the daytime, and minimal secretory activity in the early part of the night (van Cauter, 1990; Lacheline et al., 1979; Yen et al., 1995).

Both DHEA and DHEA-S are bound by serum albumin, globulins, and steroidal sex hormone binding globulin (Meikle et al., 1992; Longcope, 1995). Only a small fraction of orally administered DHEA appears in the blood at any given time as DHEA; most undergoes conversion to DHEA-S by sulfotransferases in the liver and extrahepatic tissues (Barker, 1994; Corner, 1992; Falany, 1995; Arlt, 1998). DHEA-S is converted back to DHEA by peripheral tissues containing DHEA sulfatases, including lymphocytes and macrophages. DHEA is subsequently metabolized to androstenedione as well as the potent androgens, testosterone and dihydrotestosterone, and the estrogens, estrone and estradiol. Adipose tissue may serve as a substantial reservoir for adrenal androgens. The aromatization of DHEA in peripheral tissue is thought to account for the majority of estrogen biosynthesis in postmenopausal women (Grodin et al., 1973).

The bioavailability of a drug can play an important role in its efficacy. It has been reported that DHEA occurs in at least three and as many as five anhydrous polymorphic forms and at least three hydrated forms, depending on environmental conditions and the manner of preparation (Chang et al., 1995). The known forms have been reported to be distinguishable on the basis of infrared spectroscopy and powder diffraction analysis, except that forms S3 and S4 are indistinguishable using the latter method (ibid.). Work conducted in support of the present invention indicates the existence of a sixth anhydrate form designated herein as form VI, which is detectable by solid state NMR but not by infrared spectroscopy or x-ray powder diffraction analysis.

Although DHEA is available from a variety of commercial sources, these materials show significant variation in their polymorphic compositions, which can cause variations in bioavailability due to differences of absorption during uptake in vivo.

Accordingly, it is an object of the present invention to provide DHEA formulations enriched in the form I polymorph or the form II polymorph, to achieve more consistent bioavailability and reliable efficacy. Formulations enriched in the form VI polymorph are also contemplated.

SUMMARY OF THE INVENTION

The present invention includes, in one aspect, a pharmaceutical formulation comprising dehydroepiandrosterone (DHEA), at least 85% of which is present as the form I polymorph, and at least one pharmaceutical excipient. Preferably, at least 90% of the DHEA is present as the form I polymorph, more preferably 95%, and most preferably greater than 99%. The invention also includes a composition of matter consisting essentially of the form I polymorph of DHEA.

The invention also includes, in a second general embodiment, a pharmaceutical formulation comprising DHEA, at least 85% of which is present as the form II polymorph, and at least one pharmaceutical excipient. Preferably, at least 90% of the DHEA is present as the form II polymorph, more preferably 95%, and most preferably greater than 99%.

Also included are pharmaceutical formulations comprising DHEA, at least 85% of which is present as the form VI polymorph, and at least one pharmaceutical excipient. Preferably, at least 90% of the DHEA is present as the form VI polymorph, more preferably 95%, and most preferably greater than 99%. The invention also includes a composition of matter consisting essentially of the form VI polymorph of DHEA.

The invention also includes a method for preparing a capsular or tablet formulation of DHEA. In the method, at least one solid pharmaceutical excipient is mixed with DHEA, at least 85% of which is present as a single polymorph selected from form I and form II, and the solid formulation is either placed in a capsular container suitable for oral delivery or compressed to form a tablet.

In another aspect, the invention includes a method of administering DHEA to a subject to obtain an ameliorative result, wherein a pharmaceutically acceptable amount of DHEA is administered such that at least 85% of the DHEA is present as a single polymorph selected from form I, form II, and form VI, and preferably selected from forms I and II. These methods are useful for treating a variety of medical conditions, such as systemic lupus erythematosus, loss of bone density, osteoporosis, chronic fatigue syndrome, or fibromyalgia, or in DHEA replacement therapy.

The invention also includes a method for controlling the bioavailability of a DHEA formulation. In the method, a therapeutically effective amount of a DHEA formulation is administered to a subject, where the DHEA in the formulation consists of a preselected, known ratio of DHEA polymorphs.

The compositions and methods are useful for achieving more uniform bioavailabilities in DHEA formulations than have previously been achieved, in light of the applicants' discovery that bioavailability of DHEA in vivo is dependent upon the polymorphic composition of the DHEA.

These and other objects and features of the invention will be better understood in light of the following description.

DETAILED DESCRIPTION OF THE INVENTION

I. DHEA Polymorphs

The present invention is directed to pharmaceutical preparations of DHEA having more consistent bioavailabilities and pharmacokinetic properties than preparations available prior to the invention. In one aspect, the invention is directed to pharmaceutical compositions comprising DHEA such that at least 85%, preferably at least 90%, and more preferably at least 95% to 99% of the DHEA is present as the form I polymorph. Such compositions exhibit good uptake by the GI tract upon oral administration, show good therapeutic activity, and are highly stable under ambient conditions.

In another aspect, the invention is directed to pharmaceutical compositions comprising DHEA such that at least 85%, preferably at least 90%, and more preferably at least 95% to 99% of the DHEA is present as the form II polymorph. Such compositions exhibit good uptake by the GI tract upon oral administration, a rapid rate of absorption (greater than the form I polymorph) and good therapeutic activity, and are also stable under ambient conditions.

Compositions thus enriched in form I or form II, as described herein, provide more predictable pharmacokinetic profiles than are provided by commercially available compositions having random polymorphic compositions. Compositions similarly enriched in form VI are also contemplated.

A. Preparation of DHEA Polymorphs

DHEA is known, via analytical techniques such as x-ray diffraction, infrared (IR) spectroscopy, and differential scanning calorimetry (DSC), to occur in several different hydrate and anhydrate crystal forms. The anhydrate forms include forms I, II, III, IV and V, although the latter two forms have been observed only transiently by DSC. The hydrates (solvates) include forms S1 (¼ hydrate), S2 (monohydrate), S3 (monohydrate), and S4 (½ methanolate).

DHEA, and precursors such as DHEA acetate, are commercially available from various sources (e.g., Sigma Chemical Co., St. Louis, Mo.; Aldrich Chemical Company, Inc.; Diosynth, Inc.; Pfaltz & Bauer, Inc.; Schering AG). DHEA compositions enriched for selected polymorphs can be prepared by crystallization of commercial DHEA in selected solvents under appropriate cooling or evaporation conditions. Although conditions have been reported by others for preparing the above-mentioned stable forms (Chang et al., 1995), it has been found by the present applicants that previously reported methods for preparing form I, including those described by Chang, yield products containing an additional polymorph that is designated herein as form VI. Accordingly, improved methods described herein have been developed for preparing pure form I to the exclusion of other polymorphs.

In one preferred method, pure form I is prepared by (a) crystallizing DHEA from anhydrous 2-propanol (or, alternatively, acetone or acetonitrile) under a nitrogen stream at room temperature over about 2 days, producing a crystalline precipitate that contains predominantly form I and some amount of form VI, followed by (b) suspending the precipitate in ethyl acetate (about 100 mL/30 g of DHEA) and stirring the resulting slurry at room temperature for about one week, followed by filtration. The filter cake is allowed to dry at room temperature overnight. $^{13}$C-SSNMR analysis (discussed below) showed that product prepared by this method consisted of pure or nearly pure (>99%) form I; no other forms were detected by $^{13}$C-SSNMR.

DHEA highly enriched for form II can be obtained by rapid crystallization from tetrahydrofuran (THF), dioxane, chloroform or mixtures of chloroform and THF. Example 1 provides a specific procedure for crystallization from THF, which produced a product shown by X-ray powder diffraction to be pure form II.

Other polymorphs can be prepared as follows. Form III can be obtained by desolvation of form S3 or S4 at room temperature under vacuum. Form VI can be obtained in pure form, or as a mixture with form I, by crystallization of crude DHEA (prepared by saponification of DHEA acetate, as described in Example 1, without the methanol recrystallization step) from isopropanol, without a subsequent slurrying step. Form S1 can be obtained by crystallization in methylene chloride under conditions of 50–60% relative humidity, or by grinding with methanol for 30 minutes and air drying. Form S2 can be prepared by crystallization in 40% ethanol or distilled water, or by slow evaporation in acetonitrile, acetone, ethyl acetate, or THF. Form S3 can be prepared by replacing methanol molecules of a methanol half-solvate (form S4) with water under conditions of 60% relative humidity. Form S4 (½ methanolate) can be obtained by cooling a methanol solution of DHEA. Additional procedures for preparing various polymorphs can be found in Chang et al. (1995).

B. Characterization of DHEA Compositions

In order to prepare DHEA compositions that are enriched for selected DHEA polymorphs, in accordance with the invention, it is important to be able to determine quantitatively the polymorph content of DHEA materials to establish the degree of enrichment for the desired polymorph relative to other polymorphs that may be present. Any appropriate method can be used for this purpose, provided that the method has a level of sensitivity and accuracy sufficient to permit measurement of the content of the major preferred polymorph within ±5%, and preferably within ±2.5% or less. Furthermore, it will be appreciated that a selected technique for measuring the polymorphs may not be capable of measuring all of the possible polymorphs, or it may be able to measure certain individual polymorphs only as a sum of two or more polymorphs. However, as discussed below, for measuring forms I, II and VI, these limitations either are not a concern or can be overcome by combining the results of complementary methods.

B1. X-Ray Powder Diffraction

X-ray powder diffraction, the industry standard for determining polymorphic forms of crystalline substances, can be used to measure the relative amounts of forms I+VI, II, III, S 1, S2, S3, and S4. However, this technique is not able to distinguish forms I and VI, as was shown by solid state nuclear magnetic resonance (see below).

In studies conducted in support of the present invention, essentially homogeneous samples of forms I, II, III, S1, S2, S3, and S4 of DHEA were prepared as described above. Form VI was studied as a 36:64 mixture (VI:I) with form I. Powder diffraction x-ray data were collected, as described in the Materials and Methods section below, to identify distinguishing peaks for each polymorph. The observed diffraction patterns were in general agreement with crystal structures reported previously for forms I, S1, S2, and S4 (Cox et al., 1990; Caira et al., 1995).

Table 1 summarizes the distinct reflections found for each polymorph. The relative amounts of each polymorph in a DHEA sample can be determined by integrating peak heights or peak areas of reflections that are unique to each DHEA polymorph in the sample, according to standard quantitative x-ray methods, with integration of peak areas generally being preferred.

The diffractograms for the form I sample were found to be the same as for the form I/VI mixture, indicating that x-ray diffraction alone can quantify only the sum of these polymorphs. The level of one or the other form must be independently measured by another technique, preferably solid state NMR, as described below.

TABLE 1

Unique Reflections of Polymorphs

| DHEA Form | Unique Peaks |
|---|---|
| I | 15.0 (s), 16.8 (w), 18.0 (m), 18.7 (m), 19.1 (w), 19.3 (w), 20.2 (w), 24.8 (w), 25.0 (w), 25.2 (w) |
| II | 8.6 (w), 17.3 (w), 20.9 (m), 22.0 (w), 22.2 (w), 27.1 (w) |
| III | 11.8, 12.0, 13.0, 14.8, 17.0, 24.6 |
| S1 | 13.4, 25.8 |
| S2 | 11.1, 12.4, 14.1, 19.2 |
| S3 | 14.1, 14.8, 18.2, 25.0 |
| S4 | 14.0, 14.5, 17.1 |

[a]Peak positions are given in degrees 2θ; s = strong, m = medium, w = weak.

Typically, the XRPD analysis can be simplified by visually inspecting the diffractogram to determine which polymorphs are present at detectable levels, and then limiting integration to the unique reflections corresponding to those polymorphs. Usually, for anhydrous preparations, only forms I, II and/or VI are present, to the exclusion of hydrates S1 through S4. Minor polymorph components present at levels of about 5% can be readily quantified, with a lower limit of detection of about 2%

For measuring polymorphic content of DHEA in pharmaceutical formulations containing additional materials such as pharmaceutical excipients, reflections arising from the additional materials can be subtracted out by calculating a difference pattern from diffractograms of such additional materials in the presence and absence of the DHEA.

B2. Solid State NMR (SSNMR)

Solid state $^{13}$C-NMR can also be used to detect and quantify polymorphs or crystalline substances and is a more sensitive technique than XRPD. However, as it is an expensive and time-consuming procedure, it is not routinely used. In the studies described herein, $^{13}$C-SSNMR was required to distinguish forms I and VI of DHEA, as noted above.

Unique resonance peaks that can be used to quantify polymorphs I, II, VI, and S1–S4 are provided in Table 2. In general, the various polymorphs exhibit unique resonance shifts in the regions of 10–18 ppm (low field) and 115–124 ppm (high field) (ppm relative to adamantane). However, because some of the peaks overlap in the low field region, the high field region generally provides better quantitative results.

TABLE 2

$^{13}$C-SSNMR Peak Assignments

| Form | Carbon No. 18 (ppm) | Carbon No. 6 (ppm) |
|---|---|---|
| In solution[a] | 14.9 | 120.2 |
| I | 14.8, 14.1[b] | 120.4, 118.9[b] |
| II | 13.1 | 119.9 |
| III | 15.4, 13.1 | 120.1[c] |
| VI | 14.4 | 118.5 |
| S1 | 14.3, 12.8[b] | 121.2, 119.5[b] |
| S2 | 12.6[b] | 123.4, 120.4[b] |
| S3 | 13.9 | 119.1 |
| S4 | 13.9 | 119.1 |

[a]Pouchert C. J., THE ALDRICH LIBRARY OF NMR SPECTRA, compound number 12,578-4 (1983).
[b]Known to have 2 crystallographically independent molecules in the structure.

The selected resonance peaks can be quantified by any known quantitation technique, such as the curve-fitting technique described by MacDonald (1980). Studies on mixtures of forms I and VI over a range of different concentrations showed that the responses to unique peaks for form VI are linear, indicating that the integration method is reliable for measuring the proportion of form VI in a sample relative to other polymorphs such as form I. Additional studies conducted in support of the invention established that there is good agreement for polymorph determinations by SSNMR and x-ray diffraction.

B3. Infrared Spectroscopy

Infrared spectroscopy provides yet another method for determining polymorph content of DHEA compositions. Details of this technique can be found in Chang et al. (1995). However, like x-ray diffraction, it appears that this technique does not distinguish form I from form VI.

C. Stability of DHEA Form I and Form II

A 14-day stress study monitored by XRPD showed that, at ambient temperature and 50° C., both form I and form II of DHEA are stable to solid form conversion for two weeks at relative humidities (RHs) as high as 84%. The 14-day data, given in Table 3, shows that Form I is stable for two weeks at ambient temperature and 95% RH. However, form II is converted to S2 under these conditions. At 50° C. and 95% RH, form I is converted to S2; at 50° and at RH of 75% or greater, form II is partially converted to S1. Little weight gain (<0.8%) is observed in these samples. (Weight losses observed at 50° C. could be due to loss of residual solvent, sublimation of sample, and/or thermal degradation.)

After one, two, three, and six months at either 25° C./58% RH or 40° C./75% RH, form I remained stable to solid form conversion, as shown in the Table.

In summary, forms I and II are both stable under ambient conditions and under heat at non-saturating humidity; form I exhibits greater overall stability.

TABLE 3

Stability of DHEA Forms I and II

| Polymorph | Temp | RH, % | Wt change, % (14 days) | Final Form (by XRPD), 14 days | Final Form (by $^{13}$C-SSNMR), 1, 2, 3, and 6 months |
|---|---|---|---|---|---|
| Form I | 25° C. | 58 | −0.6 | I | I |
|  |  | 75 | +0.3 | I | —(a) |
|  |  | 84 | +0.1 | I | — |
|  |  | 95 | +0.2 | I | — |
|  | 50° C. | 58 | −1 | I | — |
|  |  | 75 | −3 | I | I(b) |
|  |  | 84 | −2 | I | — |
|  |  | 95 | +1 | S2 | — |
| Form II | 25° C. | 58 | 0 | II |  |
|  |  | 75 | −0.3 | II |  |
|  |  | 84 | +0.2 | II |  |
|  |  | 95 | +5 | S2 |  |
|  | 50° C. | 58 | −1 | II |  |
|  |  | 75 | −2 | II + S1 |  |
|  |  | 84 | −0.3 | II + S1 |  |
|  |  | 95 | +1 | II + S1 |  |

(a) not determined
(b) temperature was 40° C.

II. Formulation and Administration

Formulations containing the DHEA compositions of the invention may be provided in various dosage forms, such as, for example, tablets, capsules, powders, controlled-release formulations, suspensions, emulsions, suppositories, creams, ointments, lotions, or aerosols, and are preferably provided in solid dosage forms suitable for simple administration of precise dosages.

The compositions typically include a conventional pharmaceutical carrier, or excipient, and may additionally include other medicinal agents, carriers, adjuvants, and the like. Preferably, the composition will contain about 0.5% to 75% by weight, and more preferably about 5% to 25% by weight, DHEA, with the remainder consisting of suitable pharmaceutical excipients. For oral administration, such excipients may include pharmaceutical grades of lactose, mannitol, starch, magnesium stearate, sodium saccharine, talcum, cellulose, glucose, gelatin, sucrose, magnesium carbonate, and the like.

Conveniently, the formulations of the invention can be administered orally, e.g., by capsule or tablet, for rapid uptake in the blood stream and distribution to various compartments of the body. The amount and frequency of administration will vary, depending on the patient and on the therapeutic application as detailed further below. In another approach, solid formulations can be administered as a suppository, e.g., when oral administration is contraindicated.

When the composition is employed in the form of solid preparations for oral administration, the preparations may be tablets, granules, powders, capsules or the like. For preparation of orally deliverable capsules, DHEA having the desired polymorph composition is mixed with at least one pharmaceutical excipient, and the solid formulation is placed in a capsular container suitable for delivery to the gastrointestinal tract. In preferred forms, at least 90%, more preferably at least 95%, and most preferably greater than 99% of the DHEA is present as a single polymorph selected from form I, II or VI, preferably form I or II, and most preferably form I.

For preparation of orally deliverable tablets, DHEA having the desired polymorph composition is mixed with at least one pharmaceutical excipient, and the solid formulation is compressed to form a tablet according to known methods, for delivery to the gastrointestinal tract. The tablet composition is typically formulated with additives, e.g. a saccharide or cellulose carrier, a binder such as starch paste or methyl cellulose, a filler, a disintegrator, or other additives typically usually used in the manufacture of medical preparations. The composition of the invention may also be administered to a subject transdermally or by inhalation. Methods for preparing various conventional dosage forms are known or will be apparent to those skilled in the art; for example, see *Remington's Pharmaceutical Sciences* (19th Ed., Williams & Wilkins, 1995).

III. Pharmacokinetics

As the data below demonstrate, DHEA formulations enriched for polymorph form I or form II are both absorbed well in vivo and are therapeutically active. The applicants have further discovered that commercially available supplies of DHEA can vary significantly in their polymorphic compositions, potentially resulting in significant variations in therapeutic bioavailability and efficacy. These problems are overcome by the present invention, which provides DHEA formulations of known composition having more reliable therapeutic properties, particularly consistent bioavailability.

A. Single Dose Study

Example 2 describes a study in which 34 healthy postmenopausal women were administered orally one of three formulations of DHEA, each prepared from commercially available DHEA, in capsular form. The formulations were administered in single dosages of four opaque, size 2 capsules, each capsules containing 50 mg DHEA, 152 mg lactose (169 mg for formulation 3), 108 mg corn starch, and 3 mg magnesium stearate.

The polymorphic compositions of the formulations differed as summarized in Table 4 below. Formulation 1 contained 82% form 1,0% form II, and 18% form VI, while formulation 2 contained 22% form I, 44% form II, and 33% form VI (by SSNMR). Formulation 3, fairly similar to formulation 2, contained 18% form I, 43% form II, and 39% form VI. The average particle sizes in these formulations varied according to the technique used for measurement but generally fell within a range of 50–150 μm, with the particles in formulation 1 being somewhat larger (Table 5).

TABLE 4

Polymorph Ratios in Formulations 1-3

| Formulation | [I + VI]:II Ratio (by XRPD) | I:VI:II Ratio (by SSNMR) |
|---|---|---|
| 1 | 100:0 | 82:18:0 |
| 2 | 53:47 | 22:33:44 |
| 3 | 49:51 | 18:43:39 |

TABLE 5

Particle Size

| | Formulation | | | |
|---|---|---|---|---|
| Methodology | 1 | 2 | 3 | 4 (see below) |
| Microscopy | 97 μm | 55 μm | 74 μm | — |
| Sonic Sifter Sieving | 207 μm | 180 μm | 180 μm | — |
| Malvern Light Scattering | 141 μm | 73 μm | 88 μm | 71 μm |

Figure 1:
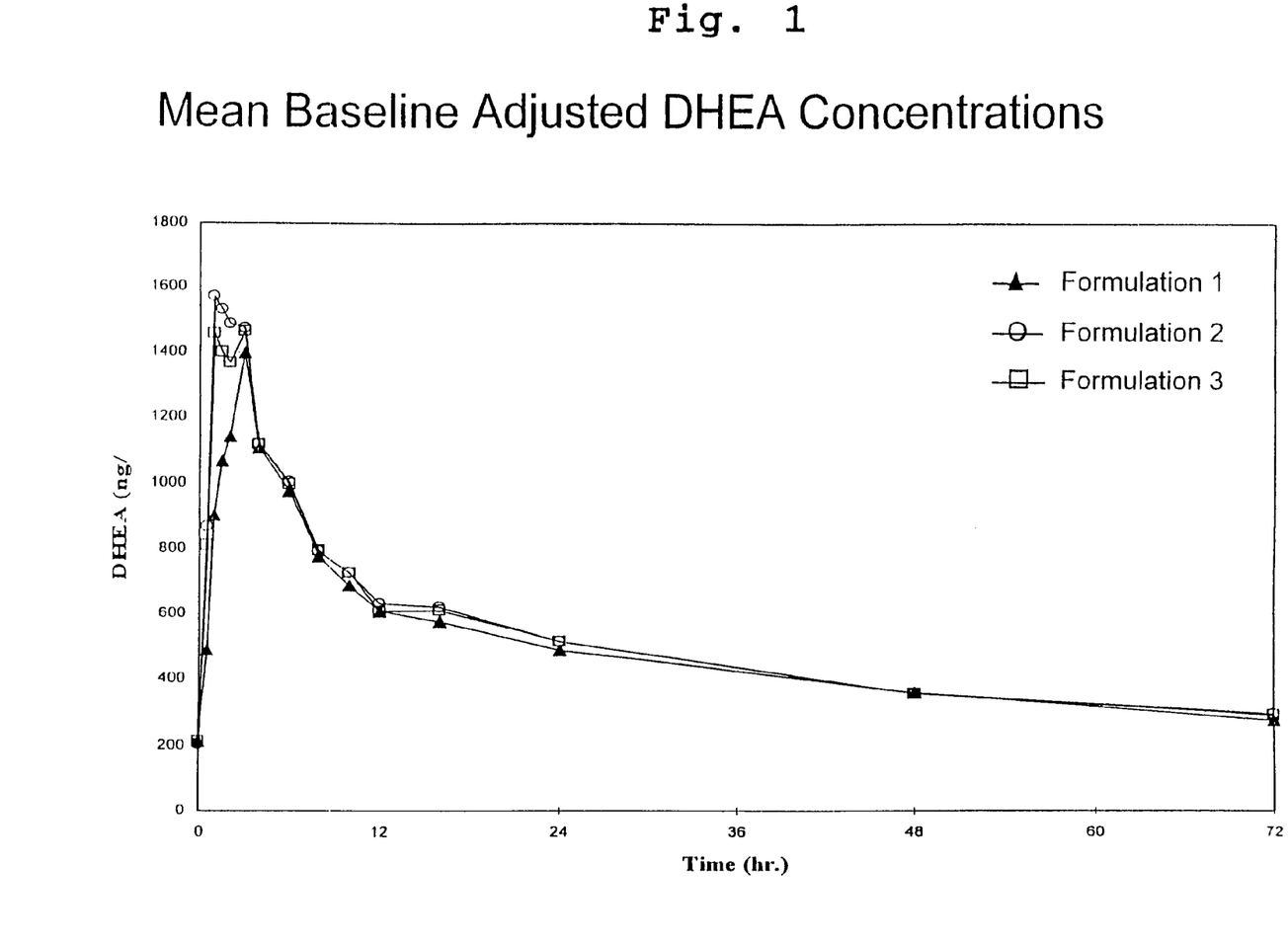
FIGS. 1 and 2 show mean baseline adjusted serum concentrations of DHEA and DHEA-S, respectively, in human subjects up to 72 hours after receiving a single dose of DHEA (formulation 1, 2 or 3, as described below) containing different proportions of DHEA forms I, II and VI.
Figure 2:
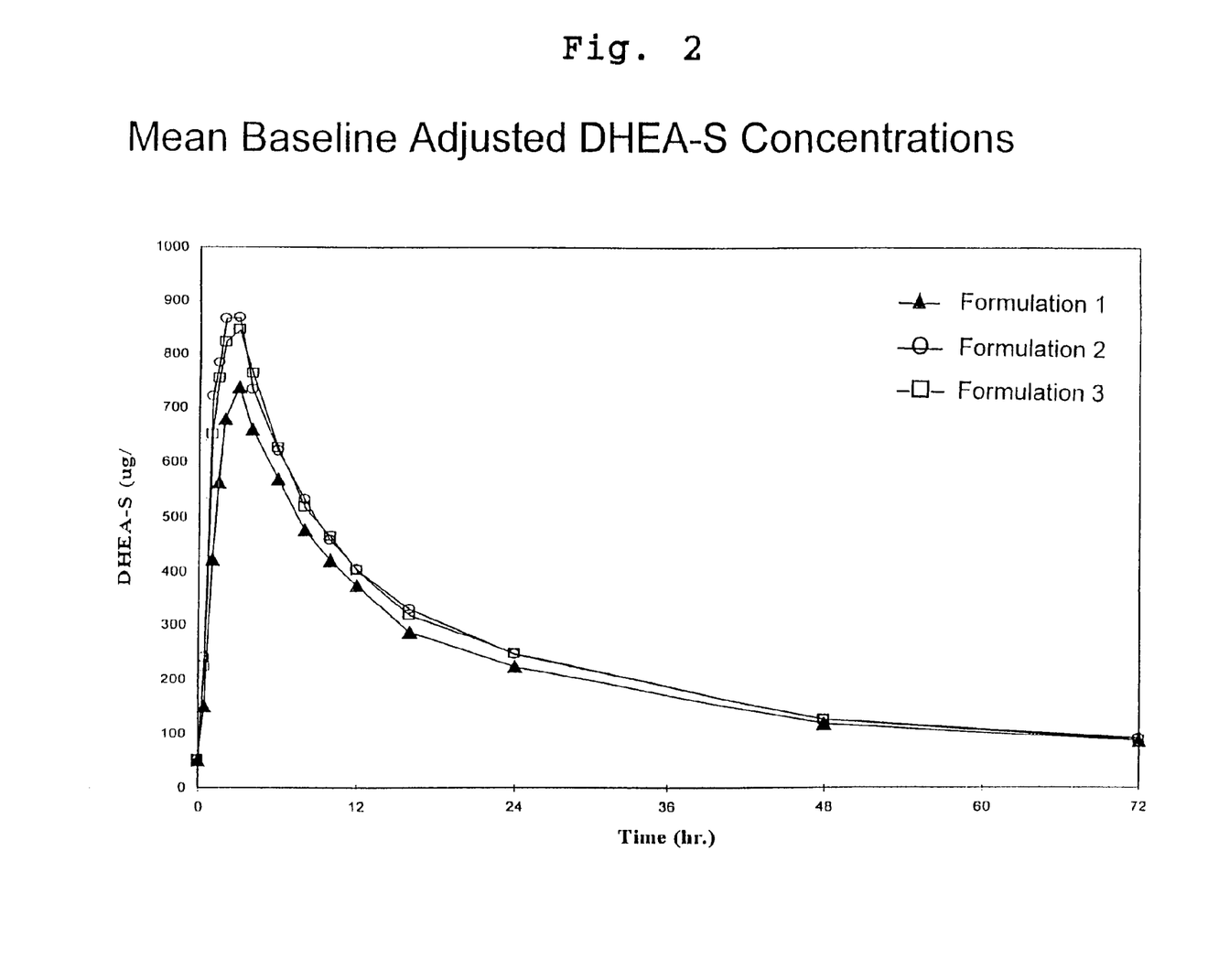

Blood samples were collected prior to and at various times after administration, and the levels of DHEA and DHEA-S were measured by immunoassay. Time plots of the levels of DHEA and DHEA-S are shown in FIGS. 1 and 2, respectively. With reference to FIG. 1, the profile for formulation 1 shows that a maximum concentration was reached about three hours after administration, followed by a somewhat rapid decline to half the maximum concentration after about 12 hours and then a gradual decline to about a third of the maximum concentration after 72 hours. Formulations 2 and 3 achieved a maximum concentration more rapidly, within about an hour of administration, followed by a 2-stage decline in concentration similar to that shown by formulation 1.

These results show that both form I and form II have high bioavailability when administered orally. The data also indicate that formulations 2 and 3, having a high proportion of form II, are absorbed more rapidly and appear to have a higher bioavailability (by about 6–14% based on AUC measurements) relative to formulation 1.

The profiles for DHEA-S showed similar patterns. All formulations reached a maximum concentration after about three hours, showing that DHEA was converted rapidly to its major metabolite, the sulfate form. The shapes of the profiles were also very similar, except that formulation showed consistently lower levels of DHEA-S than formulations 2 and 3, consistent with the results for DHEA shown in FIG. 1. The results show again that formulation 1 appears to have a lower bioavailability than formulations 2 and 3.

The estimated mean pharmacokinetic parameters (see Example 1) from this study are presented in Tables 6 and 7 below. AUC (area under curve) is an indicator of extent of absorption; $C_{max}$ and $T_{max}$ are indicators of rate of absorption. Serum DHEA concentrations for all samples were above the assay limit of quantification. Baseline-adjusted values were obtained by subtracting the day 1 pre-dosing serum concentration from each serum concentration value.

TABLE 6

Baseline Adjusted Mean Pharmacokinetic Parameters for Serum DHEA: Single Dose Study

| | Mean (Std Dev); n = 34 | | |
|---|---|---|---|
| Parameters | Formulation 1 | Formulation 2 | Formulation 3 |
| $C_{max}$ (μg/dL) | 1.25 (0.614) | 1.70 (1.07) | 1.68 (0.918) |
| $T_{max}$ (hr) | 2.78 (0.915) | 1.84 (1.16) | 2.09 (1.34) |
| $AUC_{(0-\infty)}$ (μg · hr/dL) | 24.0 (9.89) | 25.6 (10.2) | 25.2 (8.53) |
| $AUC_{(0-72)}$ (μg · hr/dL) | 19.4 (8.56) | 22.0 (8.43) | 21.1 (7.31) |

TABLE 7

Baseline Adjusted Mean Pharmacokinetic Parameters for Serum DHEA-S: Single Dose Study

| | Mean (Std Dev); n = 34 | | |
|---|---|---|---|
| Parameters | Formulation 1 | Formulation 2 | Formulation 3 |
| $C_{max}$ (μg/dL) | 732.4 (193.0) | 910.6 (251.7) | 873.2 (230.1) |
| $T_{max}$ (hr) | 2.68 (0.72) | 2.22 (0.97) | 2.32 (0.70) |
| $AUC_{(0-\infty)}$ (μg · hr/dL) | 14396 (5591) | 15851 (6461) | 15290 (5818) |
| $AUC_{(0-72)}$ (μg · hr/dL) | 12395 (4969) | 14423 (5569) | 14121 (5175) |

B. Multiple Dose Study

Example 3 describes an open-label, randomized, three period crossover pharmacokinetic study in which 39 healthy postmenopausal women were administered orally one of two formulations of DHEA in capsular form. The formulations were administered in single dosages of four opaque, size 2 capsules, each capsule containing 50 mg DHEA, 152 mg (Formulation 4) or 169 mg (Formulation 3) lactose, 108 mg corn starch, and 3 mg magnesium stearate. The DHEA polymorph composition of formulation 3 was as shown in Table 4 above (18% form I, 43% form II, and 39% form VI by SSNMR). Formulation 4 contained substantially pure (~100%) form I DHEA, prepared by methods described herein.

Dosages were administered at the same time each morning of each of two seven-day study periods, separated by a seven-day washout period. Serum samples were obtained five minutes prior to dosing on days 1 to 6, for measurement of trough levels of DHEA and DHEA-S. On day 7 of each study period, serum samples were obtained 30 minutes prior to dosing, then at various time intervals up to 72 hours post dosing, and the levels of DHEA and DHEA-S were measured by immunoassay, as described in Example 3.

Tables 8 and 9 show baseline-adjusted pharmacokinetic parameters $AUC_{144-168}$ (extent of absorption), $T_{max}$ and $C_{max}$ (rate of absorption) for the two formulations. The $AUC_{144-168}$ value represents a single dosing interval (day 7), as is standard for multidose studies.

TABLE 8

Baseline Adjusted Mean Pharmacokinetic Parameters for Serum DHEA: Multiple Dose Study

| | Mean (SD); n = 39 | |
| Parameters | Formulation 3 | Formulation 4 |
| --- | --- | --- |
| $C_{max}$ (µg/dL) | 1.04 (0.44) | 0.94 (0.66) |
| $T_{max}$ (hr) | 2.3 (0.8) | 2.5 (0.6) |
| $AUC_{144-168}$ (µg · hr/dL) | 9.011 (3.99) | 8.36 (3.67) |

TABLE 9

Baseline Adjusted Mean Pharmacokinetic Parameters for Serum DHEA-S: Multiple Dose Study

| | Mean (SD); n = 39 | |
| Parameters | Formulation 3 | Formulation 4 |
| --- | --- | --- |
| $C_{max}$ (µg/dL) | 1477 (390) | 1295 (358) |
| $T_{max}$ (hr) | 2.3 (0.7) | 2.4 (0.5) |
| $AUC_{144-168}$ (µg · hr/dL) | 15226 (5262) | 13995 (4800) |

Consistent with the results shown in the single-dose study above, formulation 4 (~100% form I) showed somewhat reduced bioavailability, in terms of rate and degree of absorption, compared to formulation 3 (mixture of polymorphs).

Figure 3:
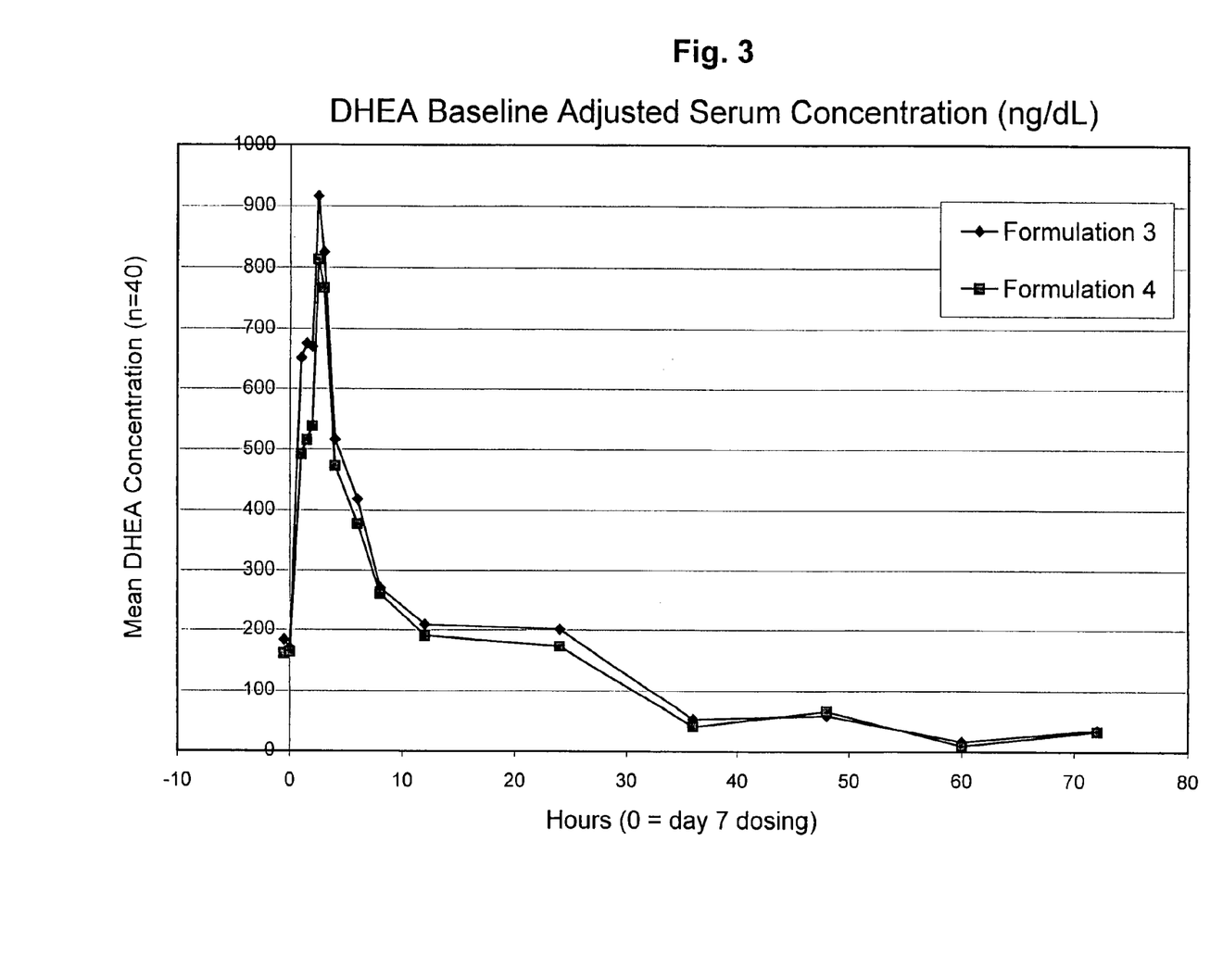
FIGS. 3 and 4 show mean baseline adjusted serum concentrations of DHEA and DHEA-S, respectively, in human subjects on days 7 to 10 of a multidose study, starting at 0.5 hours prior to dosing on day 7, using DHEA formulations, as described below, containing a mixture of forms I, II and VI (formulation 3) or pure form I (formulation 4).
Figure 4:
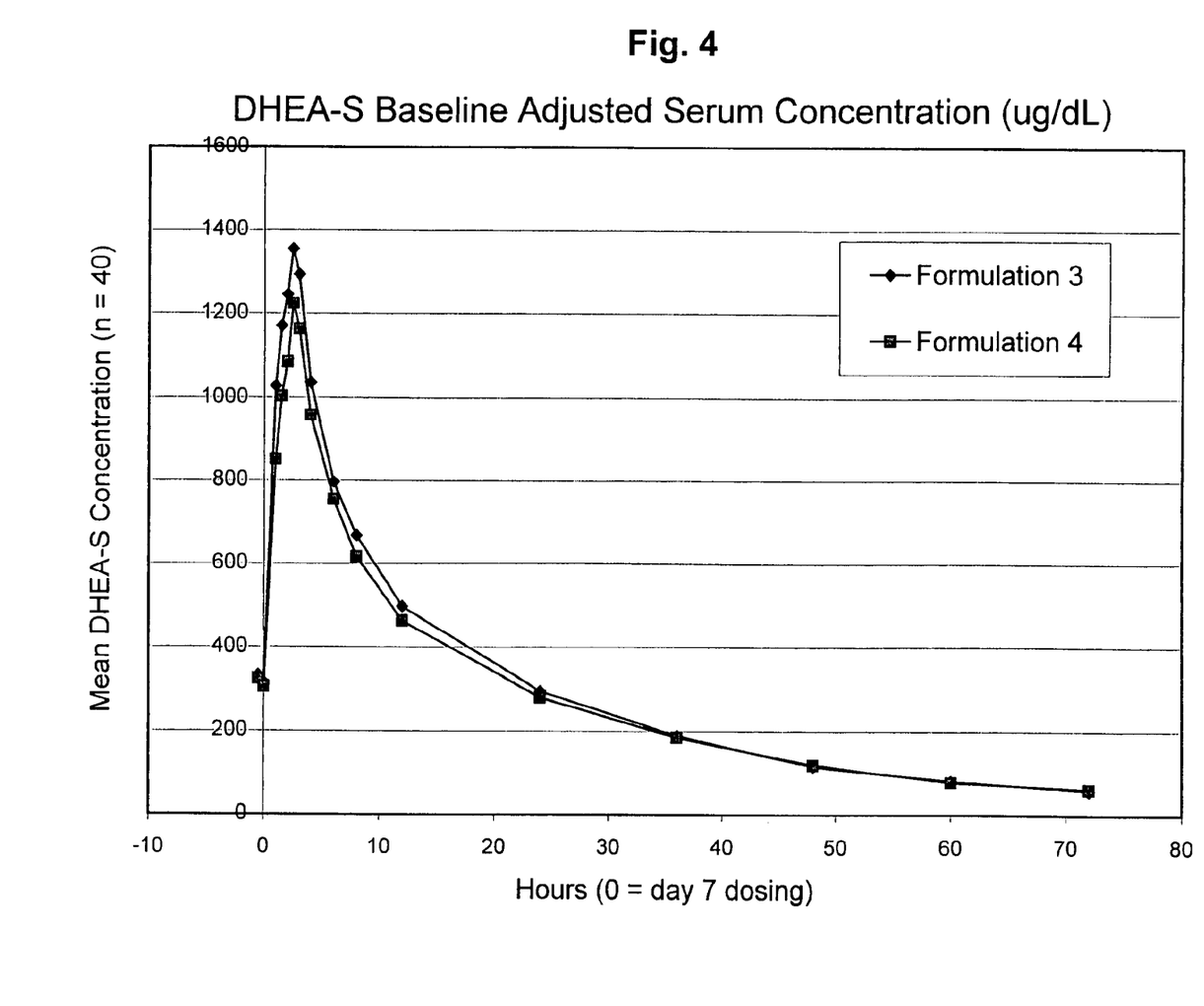

Time plots of the levels of DHEA and DHEA-S, from 0.5 hours before dosing on day 7 through day 10, are shown in FIGS. 3 and 4, respectively. Again, the plots show that, while both formulations are absorbed rapidly, formulation 3, having a high proportion of form II, is absorbed more rapidly and appears to have a higher bioavailability than formulation 4, containing pure form I.

IV. Bioequivalence in DHEA Formulations

In one aspect, the invention is directed to methods of controlling bioavailability of DHEA formulations and achieving bioequivalence between different formulations. For example, different DHEA formulations containing DHEA and excipients in the same proportions may be prepared from different batches of DHEA and thus may exhibit different bioavailabilities in vivo. As discussed above, it has been found by the inventors that, because DHEA preparations can vary significantly in their polymorph compositions (1) from different suppliers, and (2) from batch to batch from the same supplier, pharmaceutical formulations prepared from commercially available supplies of DHEA can vary significantly in their in vivo bioavailabilities.

The invention also includes a method for controlling the bioavailability of a DHEA formulation. In the method, a therapeutically effective amount of a DHEA formulation is administered such that the formulation comprises a preselected, known ratio of DHEA polymorphs. That is, a DHEA formulation is prepared having known proportions (and amounts) of one or more DHEA polymorphs, e.g., by using appropriate crystallization conditions as discussed above, or by mixing appropriate amounts of the desired polymorphs. The polymorphic ratio can be selected to provide a desired bioavailability of the DHEA, e.g., based on assessment of the bioavailability by methods such as described above and in Example 2. The method is useful for achieving more uniform and predictable bioavailabilities of DHEA formulations than have previously been achieved, in light of the applicants' discovery that bioavailability of DHEA in vivo is dependent upon the polymorphic composition of the DHEA.

V. Indications

DHEA is reported to be useful in treating many medical conditions. Exemplary conditions which can be treated include, for example, systemic lupus erythematosus (McGuire et al., U.S. Pat. No. 5,817,650), where a dose of about 25 to 500 mg/day is administered, optionally concomitantly with a glucocorticoid such as prednisone. Corticosteroids may also be used to supplement DHEA, administered at 0.25 to 2.0 mg/kg, in treatment of primary adrenal insufficiency or Addison's disease (S. S. C. Yen et al., U.S. Pat. No. 5,861,391). DHEA can also be used to enhance the immune response to viral infection (U.S. Pat. No. 5,077,284), e.g. in treatment of immunocompromised subjects, such as AIDS patients, e.g. with dosages of 400 mg/day. Diabetes can be treated by administration of 120–480 mg/kg daily, for example, or in an amount equaling approximately 0.1% to 0.4% by weight of food intake, according to Coleman et al. (U.S. Pat. No. 4,518,595).

Loss of bone density, as in osteoporosis or osteopenia, can also be treated with DHEA (see, for example, Labrie, U.S. Pat. No. 5,776,923), with a typical dose being about 32 mg/kg daily. DHEA is also effective for treatment of chronic fatigue syndrome or fibromyalgia; see, for example, White, U.S. Pat. No. 5,935,949.

Other conditions of interest and suggested dosages are summarized in the Table below. As always, optimum dosages, and frequency and duration of treatment, may vary among individual subjects and can be determined by methods known to persons skilled in the art.

TABLE 10

Selected Conditions Treatable with DHEA

| Condition or Treatment | Recommended Dosage, daily | Reference |
| --- | --- | --- |
| Inhibition of platelet aggregation (e.g. stroke, restenosis) | 100–2000 mg | D. M. Eich et al., U.S. Pat. No. 5,110,810 |
| Mild depression | 15–150 mg | A. J. Morales et al., U.S. Pat. No. 5,407,927 |
| Chronic renal failure | 400–1600 mg | W. Walser, U.S. Pat. No. 5,591,736 |
| Ischemic injury (e.g. stroke, trauma) | 2–50 mg/kg | R. A. Daynes et al., U.S. Pat. No. 5,635,496 |
| Post-reperfusion injury | 2–200 mg/kg | B. A. Araneo et al., U.S. Pat. No. 5,846,963 |
| Reduced libido | 5–50 mg/kg | F. Labrie, U.S. Pat. No. 5,855,548 |
| Pulmonary hypertension | 2–50 mg/kg | B. A. Araneo et al., U.S. Pat. No. 5,753,640 |
| Myotonic dystrophy | 50–500 mg | N. Ohsawa et al., U.S. Pat. No. 5,834,451 |
| Mast cell related allergic reactions, e.g. asthma | 2–20 mg/kg | T. Dowell et al., U.S. Pat. No. 5,859,000 |
| Arthritis | 20–400 mg oral; 800–2000 mg topical | R. F. Peat, U.S. Pat. No. 4,628,052 |
| Lowering LDL cholesterol | 100–1800 mg | J. E. Nestler et al., U.S. Pat. No. 4,920,115 |
| Retroviral infections, especially HIV | 100–600 mg | P. T. Prendergast, U.S. Pat. No. 4,956,355 |

From the foregoing, it can be seen how the objects and features of the invention are met. The invention provides pharmaceutical formulations of DHEA that are enriched for polymorph form I, form II, or form VI, preferably form I or form II, and most preferably form I. These formulations provide consistent bioavailabilities, in contrast to previously utilized DHEA formulations containing varying amounts of multiple DHEA polymorphs. Formulations enriched in DHEA form I are highly stable and provide pharmaceutical compositions that retain a constant level of DHEA activity over long periods of time (e.g., more than 1 or 2 years). Accordingly, formulations enriched in form I have long shelf-lives, which is highly desirable in a pharmaceutical product. Formulations enriched in form II are stable, though somewhat less stable than form I formulations, and can have a faster rate of absorption (and higher efficacy) in vivo than form I formulations. Accordingly, formulations enriched in form II are also therapeutically beneficial.

The invention can be further understood in light of the following examples, which illustrate but are not intended in any way to limit the invention.

EXAMPLES

Materials and Methods

X-Ray Powder Diffraction (XRPD). XRPD analyses were carried out on a Siemens D-500 X-ray Powder Diffractometer-Kristaloflex or a Shimadzu XRD-6000 X-ray powder diffractometer using Cu Kα radiation (1.5406 Å).

The Siemens instrument was equipped with an IBM-compatible interface and utilized DIFFRAC AT software (SOCABIM, 1994). Slits I and II were set at 1° and the radiation was electronically filtered by a Kevex Psi Peltier cooled silicon detector with slits III at 1° and IV at 0.15°. A continuous theta-two theta scan at 6°/min (0.4 sec/0.04° step) from 4 to 40°2θ was used. A silicon standard was analyzed each day to check the instrument alignment. Each sample was prepared by pressing a small amount of the powder onto a zero-background quartz-in-aluminum sample holder.

The Shimadzu instrument was equipped with a fine-focus X-ray tube. The tube power was set at 40 kV, 40 mA. The divergence and scattering slits were set at 1° and the receiving slit was set at 0.15 mm. Diffracted radiation was detected by an NaI scintillation detector. A theta-two theta continuous scan at 3°/min (0.4 sec/0.02° step) from 4 to 40°2θ was used. A silicon standard was analyzed each day to check the instrument alignment, and an alumina standard was analyzed each day to check the X-ray tube output. Each sample was prepared for analysis by pressing it with a spatula onto a glass or quartz sample holder.

Quantitative work (measurements of peak heights and areas) was generally done on the Shimadzu instrument. Measurements of XRPD peak heights and areas were carried out using GRAMS/32 version 5.05 running on Windows NT. For quantifying the ratio of FII to FI+FVI, theta-two theta continuous scans were performed over a selected range (e.g., from 17 to 23°2θ) at a selected scan range of from 0.5 to 3.0°/min, typically 1°/min (0.4 sec/0.02° step), three times for each sample. The XRPD files were converted to ASCII format and read into GRAMS/32 version 5.05 running on Windows NT. For each scan, the peak areas and heights of a unique form I peak (typically either 18.5 or 20.2°2θ) and a unique form II peak (typically 20.8°2θ as measured over 20.5–21.2°2θ) were measured. A standard curve was generated using standardized mixtures of FI and FII ranging from 0 to 100% FII in FI at 10% intervals, except that a sample containing 5% FII was also included. The three heights (or areas) measured for each sample were averaged, and the averages were input into the equation defined by the calibration curve.

Solid State NMR Method (SSNMR). SSNMR spectra were obtained on a General Electric Omega PSG, 100 MHz spectrometer using about 50 mg of sample in a 5-mm diameter zirconia rotor. High-power proton decoupling and cross-polarization with magic-angle spinning at approximately 5 kHz were used. The magic angle was adjusted using the Br signal of KBr by detecting the side bands as described by Frye and Maciel, 1982. The chemical shifts were referenced externally to the CH resonance of adamantane at 29.50 ppm. Curve fitting of selected peaks for integration was performed as described by MacDonald (1980). The following peaks were used to measure forms I, II and VI: sum of peaks at 118.8 and 120.3 ppm (form I), peak at 119.8 ppm (form II), and peak at 118.5 ppm (form VI).

Determination of Polymorph Content. In order to determine the amounts of the various possible polymorphs of DHEA in DHEA-containing materials, the following 3-step approach was used.
1. Visual examination of an XRPD pattern to qualitatively confirm that only anhydrous forms are present.
2. Quantitative XRPD analyses to determine the amount of form FII present in a mixture of forms FI, FII, and/or FVI.
3. Quantitative SSNMR analyses to determine the amount of forms FI and FVI present.

Example 1

Preparation of DHEA and Polymorphs I and II

Synthesis of DHEA. DHEA was prepared from DHEA acetate (obtained from Diosynth, Chicago, Ill. or Berlichem, Montville, N.J.) by saponification using potassium carbonate in methanol. The product was dissolved in 6 parts methanol at reflux, and charcoal was added and removed by filtration. The methanol was evaporated until a volume of 3 parts remained, and the solution was cooled to 15° C., maintained at this temperature for 1 hour, and filtered. The wet product was refluxed with 8.5 parts of water to remove the methanol, filtered, and dried under vacuum at 90° C. The loss on drying specification for the final product was ≦0.5%, and the specification for residual methanol was ≦0.01%.

Preparation of Form I. Thirty grams of DHEA, as prepared above, were placed in a 500 mL flask under a nitrogen atmosphere. Anhydrous 2-propanol (isopropanol) was added until all the DHEA dissolved. The resulting solution was stirred under a nitrogen flow for 2 days, at which time all of the solvent had evaporated. SSNMR analysis indicated that the product contained a mixture of forms I and VI, with form I predominating. To convert the form VI component to form I, the product (about 30 g) was added to about 100 mL of ethyl acetate, and the resulting slurry was stirred at ambient temperature for 1 week and filtered. The filter cake was allowed to dry under ambient conditions overnight and then passed through a single sieve (75 μm), yielding 9.0 g of particles with sizes >75 μm and 3.2 g of particles with sizes <75 μm. $^{13}$C-SSNMR analysis of the fraction with particle size >75 μm showed that only form I was present.

Preparation of Form II. Thirty grams of DHEA were placed in a 500 mL flask under a nitrogen atmosphere. Anhydrous tetrahydrofuran was added until all the DHEA dissolved. The resulting a solution was stirred under a nitrogen flow for 3 days, at which time all of the solvent had evaporated. The solid was removed from the flask and found by XRPD analysis to be solely form II (Siemens diffractometer).

Example 2

Pharmacokinetics of Orally Administered DHEA Formulations: Single Dose Study

This study was an open-label, randomized, three period crossover pharmacokinetic study in 34 healthy postmenopausal women. Subjects were contacted the evening prior to each dosing visit and reminded to begin an overnight fast, with nothing to eat or drink (no water permitted) for 10 hours prior to dosing. Serum samples for measurement of DHEA and DHEA-S were drawn thirty minutes prior to dosing and at 0, 0.5, 1, 1.5, 2, 3, 4, 6, 8, 10, 12, 16, 24, 48 and 72 hours after the subjects had received a 200 mg oral dose of DHEA (4 capsules of formulation 1 or 2) with 8 oz. of water. Each dosing period was followed by a 7 day washout period before the next administration.

DHEA levels were determined by radioimmunoassay (RIA) at Endocrine Sciences Inc., after non-polar solvent extraction. Method validation data demonstrated a recovery range of 92–99%, a limit of detection (LOD) of 18.9 ng/dL, a limit of quantitation (LOQ) of 87.5 ng/dL, intra-assay precision ≦5%, and inter-assay precision ≦10%. Internal assay controls were monitored via control charts. DHEA-S levels were determined by radioimmunoassay (RIA) at Endocrine Sciences Inc., after enzymolysis of DHEA-S. Method validation data demonstrated recovery range 86–106%, limit of detection (LOD) 3.6 μg/dL, intra-assay precision ≦7%, and inter-assay precision ≦10%. Internal assay controls were monitored via control charts.

Each capsule contained 50 mg DHEA (formulation 1, 2 or 3) and excipients consisting of 152 mg lactose (169 mg for formulation 3), 108 mg corn starch, and 3 mg magnesium stearate. The DHEA polymorph contents of formulations 1–3 are listed in Table 4 in Section III above. The formulations were prepared in bulk amounts (e.g., 150 kg) by weighing and sieving all individual components through a size 14 stainless steel mesh screen to de-lump. All components except magnesium stearate were blended together for at least 10 minutes using a Patterson-Kelly Twin Shell 10 cubic ft dry V-blender. Magnesium stearate was added and blended into the mixture for at least 5 minutes. Homogeneity was verified by taking samples from different regions of the blender and quantifying the DHEA content on a weight basis by HPLC (isocratic, 1 mL/min 45:45:10 acetonitrile:water: methyl t-butylether, Synchropak column (C18 RP-P-100, 5 micron, 250×4.6 mm i.d. from Thinchrom, Inc., Lafayette, Ind.). After weighing, the blend was placed in opaque size 2 gelatin capsules (Capsugel or Shionogi) with 313 mg fill-weights.

Generation of Pharmacokinetic Data and Statistical Analysis: Microsoft® Excel, SAS® and WinNonlin® were used for dataset generation, statistical analysis, and pharmacokinetic (PK) evaluation of patient data.

Adjusted serum levels were calculated by subtracting baseline (average of −0.5 hr and 0 hr serum levels). Any adjusted value less than zero was set to zero. For DHEA and DHEA-S, the peak serum concentration ($C_{max}$) and time to peak concentration ($T_{max}$) were assessed from the concentration-time data. The maximal observed serum DHEA and DHEA-S concentration ($C_{max}$) and the corresponding sampling times ($T_{max}$) were determined for all treatments; $T_{max}$ is expressed in hours following the commencement of each treatment.

DHEA and DHEA-S AUC (area under curve) values were determined by the linear trapezoidal method from hour 0 to hour 72 ($AUC_{(0-72)}$) or the last measurable concentration. The area under the concentration time curve from zero to infinity ($AUC_{0-\infty}$) was determined using the following equation:

$$AUC_{0-\infty} = AUC_{0-t} + C_{last}/k_{el}$$

where $AUC_{0-t}$ is the area under the concentration-time curve from zero to the last measurable concentration ($C_{last}$) as determined by the linear trapezoidal method and $k_{el}$ is the terminal elimination rate constant. The terminal elimination rate constant was determined by using linear regression of the individual log concentrations versus time during the terminal elimination phase. The elimination rate constant was estimated by performing a regression of the natural logarithm of the concentrations on sampling time, for times in the specified range. Regressions were repeated first using the last three points, then the last four points. The half-life ($t_{1/2}$) can be calculated by dividing 0.693 by $k_{el}$.

The main pharmacokinetic parameters used to describe DHEA and DHEA-S pharmacokinetics during treatments are the area under serum concentration curve from hour 0 to hour 72 ($AUC_{(0-72)}$), the maximum serum concentration ($C_{max}$), and the time to maximum serum concentration ($T_{max}$). Comparisons of these parameters were made with an analysis of variance (ANOVA) model using the PROC GLM software (PC SAS, version 6.10).

Example 3

Pharmacokinetics of Orally Administered DHEA Formulations: Multiple Dose Study

This study was an open-label, randomized, steady-state, two-treatment cross-over study of DHEA pharmacokinetics/pharmacodynamics in healthy postmenopausal females. DHEA was administered on each of 7 days of two study periods, with an intervening 7-day washout period (Days 1 to 7 and Days 15 to 21). Subjects received a single 200 mg oral dose (four 50 mg capsules) of DHEA at the same time each morning for the 7 days of each study period. Subjects were instructed to fast for 10 hours prior to each DHEA dose. Each capsule contained 50 mg of DHEA and pharmaceutical excipients (169 mg (Formulation 3) or 152 mg (Formulation 4) lactose, 108 mg corn starch, and 3 mg magnesium stearate) to result in a total capsule fill weight of 330 and 313 mg for formulations 3 and 4, respectively. Subjects were randomized to receive one of the two formulations during each study period. The DHEA polymorph composition of formulation 3 was as shown in Table 4 above (18% form I, 43% form II, and 39% form VI). Formulation 4 contained substantially pure (~100%) form I DHEA, prepared by methods described herein.

Serum samples for the measurement of trough levels of DHEA and DHEA-S were obtained five minutes prior to the 200 mg oral dose of DHEA on days 1 to 6 of each study period.

On day 7 of each study period, each subject received the same breakfast (2 hours after dosing), lunch (6 hours after dosing) and dinner (10 hours after dosing). A full pharmacokinetic study was conducted, with serum samples for the measurement of DHEA and DHEA-S obtained 30 minutes prior to dosing and at 0, 1, 1.5, 2, 2.5, 3, 4, 6, 8, 12, 24, 36, 48, 60 and 72 hours following dosing.

DHEA levels were determined by radioimmunoassay (RIA) at Quest Diagnostics Inc. at Nichol's Institute. Method validation data demonstrated the lower limit of quantitation (LL0Q) to be approximately 10 ng/dL. Pharmacokinetic data was generated and statistical analysis carried out essentially as described for Example 2, above. The estimated mean pharmacokinetic parameters for serum DHEA and DHEA-S concentrations from this study are summarized in Tables 8 and 9, above (Section 111B).

While the invention has been described with reference to specific methods and embodiments, it will be appreciated that various modifications can be made without departing from the spirit of the invention.

The invention claimed is:

1. A pharmaceutical formulation comprising dehydroepiandrosterone (DHEA), at least 85% of which is present as the form I polymorph, and at least one pharmaceutical excipient.

2. The formulation of claim 1, wherein at least 90% of said dehydroepiandrosterone (DHEA) is present as the form I polymorph.

3. The formulation of claim 1, wherein at least 95% of said dehydroepiandrosterone (DHEA) is present as the form I polymorph.

4. The formulation of claim 1, wherein at least 99% of said dehydroepiandrosterone (DHEA) is present as the form I polymorph.

5. A method for preparing a solid DHEA formulation, said method comprising:
mixing at least one solid pharmaceutical excipient with dehydroepiandrosterone (DHEA), at least 85% of which is present as the form I polymorph.

6. The method of claim 5, wherein at least 90% of said dehydroepiandrosterone (DHEA) is present as the form I polymorph.

7. The method of claim 5, wherein at least 95% of said dehydroepiandrosterone (DHEA) is present as the form I polymorph.

8. The method of claim 5, wherein at least 99% of said dehydroepiandrosterone (DHEA) is present as the form I polymorph.

9. The method of claim 5, further comprising the step of placing the solid formulation into a capsular container suitable for delivery to the gastrointestinal tract.

10. The method of claim 5, further comprising the step of compressing the solid formulation to form a tablet.

11. A pharmaceutical formulation comprising dehydroepiandrosterone (DHEA), at least 85% of which is present as the form I polymorph as determinable by solid state 13C NMR spectroscopy, and at least one pharmaceutical excipient.

12. A pharmaceutical formulation comprising dehydroepiandrosterone (DHEA), greater than 95% of which is present as the form I polymorph as determinable by solid state 13C NMR spectroscopy, and at least one pharmaceutical excipient.

13. A method for preparing a solid DHEA formulation, said method comprising:
mixing at least one solid pharmaceutical excipient with dehydroepiandrosterone (DHEA), at least 85% of which is present as the form I polymorph as determinable by solid state 13C NMR spectroscopy.

14. A method for preparing a solid DHEA formulation, said method comprising:
mixing at least one solid pharmaceutical excipient with dehydroepiandrosterone (DHEA), greater than 95% of which is present as the form I polymorph as determinable by solid state 13C NMR spectroscopy.

* * * * *